(12) United States Patent
Banke

(10) Patent No.: US 12,241,784 B2
(45) Date of Patent: *Mar. 4, 2025

(54) ANALYTE DETECTION APPARATUS AND METHOD OF DETECTING AN ANALYTE

(71) Applicant: RSP SYSTEMS A/S, Odense (DK)

(72) Inventor: Stefan Ovesen Banke, Nyborg (DK)

(73) Assignee: RSP SYSTEMS A/S, Odense S (DK)

( * ) Notice: Subject to any disclaimer, the term of this patent is extended or adjusted under 35 U.S.C. 154(b) by 57 days.

This patent is subject to a terminal disclaimer.

(21) Appl. No.: 17/990,139

(22) Filed: Nov. 18, 2022

(65) Prior Publication Data

US 2023/0080810 A1 Mar. 16, 2023

Related U.S. Application Data

(63) Continuation of application No. 16/467,362, filed as application No. PCT/EP2017/077150 on Oct. 24, 2017, now Pat. No. 11,815,398.

(30) Foreign Application Priority Data

Dec. 6, 2016 (GB) ...................................... 1620708

(51) Int. Cl.
*G01J 3/44* (2006.01)
*A61B 5/00* (2006.01)
(Continued)

(52) U.S. Cl.
CPC .............. *G01J 3/44* (2013.01); *A61B 5/0075* (2013.01); *A61B 5/14532* (2013.01);
(Continued)

(58) Field of Classification Search
CPC .......... G01J 3/44; G01J 3/0256; G01J 3/0264; G01J 3/0272; G01J 3/1256; G01J 3/2803;
(Continued)

(56) References Cited

U.S. PATENT DOCUMENTS 4,997,281 A 3/1991 Stark
5,424,826 A 6/1995 Kinney
(Continued)

FOREIGN PATENT DOCUMENTS

EP 0 637 742 A1 2/1995
JP H07-49309 A 2/1995
(Continued)

OTHER PUBLICATIONS

Le Coarer, Etienne, et al. "Wavelength-scale stationary-wave integrated Fourier-transform spectrometry." Nature Photonics 1.8 (2007): 473-478. (Year: 2007).*

(Continued)

*Primary Examiner* — Dominic J Bologna
(74) *Attorney, Agent, or Firm* — Pillsbury Winthrop Shaw Pittman LLP

(57) ABSTRACT

An analyte detection apparatus includes a radiation source for irradiating a sample and a receiver to receive an optical Raman spectrum of radiation transmitted back from the sample, the spectrum including one or more parts of significance to an analyte to be detected and one or more parts not of significance to an analyte to be detected. The receiver includes different types of analysis device each arranged to receive a selected part of the spectrum. The different types of analysis device include at least one analysis device having high resolution and/or high signal to noise ratio for detecting a part of the spectrum of significance to the analyte to be detected and at least one second type of analysis device which provides lower resolution and/or lower signal-to-noise ratio, for detecting a part of the spectrum not of significance to the analyte to be detected.

18 Claims, 3 Drawing Sheets

(51) Int. Cl.

| | | |
|---|---|---|
| *A61B 5/145* | (2006.01) | |
| *A61B 5/1455* | (2006.01) | |
| *G01J 3/02* | (2006.01) | |
| *G01J 3/12* | (2006.01) | |
| *G01J 3/18* | (2006.01) | |
| *G01J 3/28* | (2006.01) | |
| *G01J 3/36* | (2006.01) | |
| *G01N 21/65* | (2006.01) | |

(52) U.S. Cl.
CPC ........ *A61B 5/14546* (2013.01); *A61B 5/1455* (2013.01); *G01J 3/0256* (2013.01); *G01J 3/0264* (2013.01); *G01J 3/0272* (2013.01); *G01J 3/1256* (2013.01); *G01J 3/2803* (2013.01); *G01J 3/36* (2013.01); *G01N 21/65* (2013.01); *G01N 21/658* (2013.01); *G01J 2003/1213* (2013.01); *G01J 2003/1239* (2013.01); *G01J 3/18* (2013.01)

(58) Field of Classification Search
CPC ........ G01J 3/36; G01J 3/18; G01J 2003/1213; G01J 2003/1239; A61B 5/0075; A61B 5/14532; A61B 5/14546; A61B 5/1455; G01N 21/65; G01N 21/658
See application file for complete search history.

(56) References Cited

U.S. PATENT DOCUMENTS

| 5,701,005 | A | 12/1997 | Meyers | |
|---|---|---|---|---|
| 7,511,255 | B2 | 3/2009 | Fujita | |
| 9,664,563 | B2 | 5/2017 | Lucey | |
| 10,718,668 | B2 | 7/2020 | Gu et al. | |
| 11,815,398 | B2 * | 11/2023 | Banke | A61B 5/1455 |
| 2005/0264808 | A1 * | 12/2005 | Wang | G01N 21/65 |
| | | | | 356/328 |
| 2006/0262303 | A1 | 11/2006 | Bonne et al. | |
| 2013/0289414 | A1 | 10/2013 | Adibnazari et al. | |

FOREIGN PATENT DOCUMENTS

| JP | H11-190695 | A | | 7/1999 |
|---|---|---|---|---|
| JP | 2002-085385 | A | | 3/2002 |
| JP | 2002098636 | A | * | 4/2002 |
| JP | 2013-517465 | A | | 5/2013 |
| WO | WO 2005/038437 | A2 | | 4/2005 |
| WO | WO 2008/026138 | A2 | | 3/2008 |
| WO | WO 2011/086357 | A | | 7/2011 |
| WO | WO 2012/019102 | A2 | | 2/2012 |
| WO | WO 2016/023578 | A1 | | 2/2016 |
| WO | WO 2016/034448 | A1 | | 3/2016 |

OTHER PUBLICATIONS

Wróbel, M. S. "Non-invasive blood glucose monitoring with Raman spectroscopy: prospects for device miniaturization." IOP Conference Series: Materials Science and Engineering. vol. 104. No. 1. IOP publishing, 2016. (Year: 2016).*
English machine translation of JP2002098636A (Year: 2002).*
Notice of Allowance as issued in U.S. Appl. No. 16/467,362, dated Jul. 18, 2023.
Preliminary Notice of Reasons for Rejection as issued in Japanese Patent Application No. 2019-531235, dated Apr. 5, 2022.
LineSpec™ CMOS and CCD Array Spectrometers, 2016 PT SERVIAM ABADIMURNI, [retrieved on Feb. 17 2022]. Retrieved from the Internet: <https://web.archive.org/web/20160321114918/http://saphotonics.com/products/spectroscopy-systems/linespec-cmos-and-ccd-array-spectrometers/>, (Year: 2016).
Sellar, R.G.., et al., Boreman GD. "Comparison of relative signal-to-noise ratios of different classes of imaging spectrometer," Applied optics. Mar. 21, 2005 ;44(9): 1614-24 (Year: 2005).
Le Coarer, E., et al. "Wavelength-scale stationary-wave integrated Fourier-transform spectrometry," Nature Photonics 1.8 (2007): 473-478 (Year: 2007).
International Search Report as issued in International Patent Application No. PCT/EP2017/077150, dated Feb. 12, 2018.
Wróbel, M. S., "Non-invasive blood glucose monitoring with Raman spectroscopy: prospects for device miniaturization," 39th International Microelectronics and Packaging IMAPS Poland 2015 Conference, IOP Conf. Series: Materials Science and Engineering, vol. 104, Jan. 2016, XP055432416, 10 pages.
VersaChrome Edge™ Tunable Filters, IDEX Health and Science, Retrieved from the Internet: URL: <https://www.semrock.com/versachrome-edge-tunable-filters.aspx>, Retrieved on Jun. 6, 2019.
Continuously Variable Filters (A.K.A. Linear Variable Filters), delta optical thin film, Retrieved from the Internet: URL: <https://www.deltaopticalthinfilm.com/products-old/linear-variable-filters/>, Retrieved on Jun. 6, 2019.
Microscopy Resource Center, Olympus Corporation, Retrieved from the Internet: URL: <http://www.olympusmicro.com/primer/techniques/confocal/aotfintro.html>, Retrieved on Jun. 6, 2019.
Non-Final Office Action as issued in U.S. Appl. No. 16/467,362, dated Dec. 22, 2022.

* cited by examiner

ANALYTE DETECTION APPARATUS AND METHOD OF DETECTING AN ANALYTE

CROSS-REFERENCE TO RELATED APPLICATIONS

This application is a continuation of application Ser. No. 16/467,362 filed on Jun. 6, 2019, which is the U.S. National Stage of PCT/EP2017/077150, filed Oct. 24, 2017, which in turn claims priority to Great Britain patent application number 1620708.6 filed Dec. 6, 2016. The content of these applications are incorporated herein by reference in their entireties.

FIELD

The present invention relates to an analyte detection apparatus and a method of detecting an analyte.

BACKGROUND

The use of Raman spectroscopy for the transdermal in vivo measurement of glucose or other analyte present in skin is known. In our co-pending international application WO-A-2016/034448, there is described the use of a confocal detector apparatus having at least one component expected for measuring the concentration of glucose in interstitial fluid by irradiating the skin of a user with optical radiation and then detecting and measuring the Raman scattered radiation from the sample. The device works well and provides a means for non-invasive measurement of the blood glucose level within a user's interstitial fluid, which correlates with the blood glucose level.

Most known systems that use Raman spectroscopy to measure or determine analyte concentration are often bulky and stationary. In the field of blood sugar determination using Raman spectroscopy, miniaturisation is desirable since when provided in a suitably miniaturised form, the devices will become convenient and easy to use for diabetics who often need to determine their blood sugar levels (directly or otherwise) numerous times during a single day.

WO2012019102 discloses a portable Raman diagnostic system. The system relates to the selection of the specific filter combinations, which can provide information for multivariate calibration to extract analyte concentrations in biological systems. The system of WO2012019102 utilises methods of wavelength interval selection to try and minimise size of a testing device. A plurality of wavelength selection methods and miniaturized spectroscopic apparatus designs and the necessary tools to map from one domain (wavelength selection) to the other (design parameters) are disclosed.

In the article entitled "Non-invasive Blood Glucose Monitoring with Raman Spectroscopy: Prospects for Device Miniaturisation", by M. S. Wrobel published as part of the 39th International Microelectronics and Packaging (IMAPS) Poland 2015 conference, there is disclosed the use of a plurality of photodetectors for detecting optical signals at specified wavelengths within a received Raman spectrum.

U.S. Pat. Nos. 5,701,005, 7,511,255, 5,424,826, US-A-2006/0262303, US-A-2013/0289414, and U.S. Pat. No. 4,997,281 disclose optical systems including spectrometers and/or optical filtration devices. A number of these are used within systems that rely upon Raman spectroscopy to determine information about a sample.

Examples of other analytes or metabolites, for which a miniaturised Raman device would be useful for measuring concentrations of include any one or more of lactate, fatty acids, urea, carbamide, cholesterol, or hemoglobin.

SUMMARY

According to a first aspect of the present invention, there is provided an analyte detection apparatus, the apparatus comprising a radiation source for irradiating a sample; a receiver, to receive an optical spectrum of radiation transmitted back from the sample in response to the received radiation from the source, wherein the receiver comprises a plurality of different types of analysis device each arranged to receive a selected part of the received optical spectrum transmitted back from the sample. The optical spectrum of radiation transmitted back from the sample will typically be a Raman spectrum.

An analyte detection apparatus is provided that includes more than a single type of analysis device. This means that different parts of a received spectrum can be fed or coupled to correspondingly different types of analysis device and in particular to analysis devices that might have different levels of resolution and/or signal-to-noise ratio. Thus, parts of a received spectrum that are considered significant to the analyte in question can be coupled to a first type of analysis device which has high resolution and/or high signal to noise ratio, whereas a part of the spectrum about which less detailed information is required, can be coupled to a second type of analysis device which provides lower resolution and lower signal-to-noise ratio.

This means that overall an apparatus can be provided that give as an output sufficient detail and level of data about an analyte without requiring a plurality of high resolution analysis devices. This means that the overall apparatus can be made smaller and/or less expensively without resulting in it providing an unacceptably low quality or resolution of output data. In other words the same level of high quality data can be provided about the parts of the spectrum that are considered important, whilst the apparatus used to provide it can be made more simply, at lower cost and to be smaller in physical size.

In other words, the present apparatus has the potential to enable further miniaturisation of a Raman spectroscopy based blood sugar machine. This is advantageous for diabetics or other patients who might want to measure their blood sugar and would benefit from a device that is conveniently portable.

In an embodiment, the apparatus comprises one or more filtration devices arranged to filter the received optical spectrum and direct designated components to particular ones of the plurality of different types of analysis devices.

The use of filtration devices enables the received spectrum to be easily and efficiently separated into desired components or wavelength regions. This then enables the direction of each spectral sub-region to the correct and designated analysis device. Thus, the received spectrum is subdivided into regions by the filtration elements and then each subdivided region is routed to a particular analysis device.

In an embodiment, the filtration devices include at least one tunable filtration device. Providing tunable filtration devices enables selective configuring of the apparatus so it can be tuned to be able to analyse a desired analyte. Each analyte that might be investigated will have its own Raman spectrum and so the regions of interest within the overall received spectrum might be different.

In an embodiment, the tunable filtration element comprises a filtration element that is tunable by variation in the angle of incidence (AOI) upon the filtration device. In another embodiment, the tunable filtration element comprises a filtration element that is tuned by filter displacement (linear variable filters). In such filters, the transmission window shifts with respect to the lateral position of the filter. In another embodiment, acousto-optically (electrically) tunable filters are used. In some embodiments any combination of different types of filtration elements can be used.

A further example is a filtration element in which the refractive index of a crystal is modulated periodically by a high frequency acoustic wave generated by a piezoelectric transducer. In such devices, the frequency of the wave produced by the piezo-electric transducer determines the refractive index modulation period, and thereby the wavelength of diffracted light.

In an embodiment, the different analysis devices include at least one CCD-based spectrometer.

In an embodiment, the different analysis devices include at least one CMOS-based spectrometer.

According to a second aspect of the present invention, there is provided a method of detecting an analyte, the method comprising irradiating a sample with optical radiation; receiving an optical spectrum of radiation transmitted back by the sample in response to the received radiation from the source; selectively coupling different parts of the received spectrum to different analysis devices. The optical spectrum of radiation transmitted back from the sample will typically be a Raman spectrum.

In an embodiment, the method comprises filtering the received spectrum into two or more components and coupling a first of the components to a first analysis device and a second of the components to a second analysis device.

In an embodiment, the first analysis device is a CCD-based spectrometer.

In an embodiment, the second analysis device is a CMOS-based spectrometer.

BRIEF DESCRIPTION OF THE DRAWINGS

Embodiments of the present invention will now be described in detail with reference to the accompanying drawings, in which.

DETAILED DESCRIPTION

As is known, the basis for a spectroscopic setup is a light source such as a laser, which is used for illuminating a sample. The light from the light source will interact with the sample and often result in an alteration of the light which is transmitted through, emitted by, reflected by and/or scattered by the sample. By collecting the altered light and analysing its spectral distribution, information about the interaction between the incoming light and the sample can be obtained. Hence, information about the molecular components within the sample can be obtained.

One mode of interaction between the incident light and the molecular components is Raman scattering in which there is energy exchange between the molecules and the photons of incoming light. The frequencies, i.e. the spectral distribution of the Raman scattered light will be different from that of the incoming light and uniquely reflect the specific vibrational levels of the molecule; hence it is a fingerprint spectrum. This can be used for identification of the molecular composition of the substance probed and/or the concentration of the specific molecules in the substance.

The spectrum transmitted back from the sample may be termed a received optical spectrum as it is received by a receiver and can then be processed or analysed to obtain information about the sample.

In our co-pending application WO-A-2016/034448 there is described the optical configuration and arrangement that enables results to be achieved by specifying amongst other factors, the depth within a sample from which detected radiation will be analysed. Indeed, as explained WO-A-2016/034448 teaches that ensuring that the Raman scattered light that is collected for measurement originates at or close to a specific depth within the skin can provide some advantages.

The entire contents of WO-A-2016/034448 are incorporated herein by reference, including, but not limited to the specific aspects relating to the depth within a sample from data is retrieved and the optical and physical configuration of the interface or lensing between a sample and the device.

The spectral distribution of the received optical spectrum is typically measured by using a spectrophotometer. A spectrophotometer is an optical apparatus that works by separating the light beam directed into the optical apparatus into different frequency components and subsequently measuring the intensity of these components by using analysis devices such as CCD detectors or CCD arrays.

Figure 1:
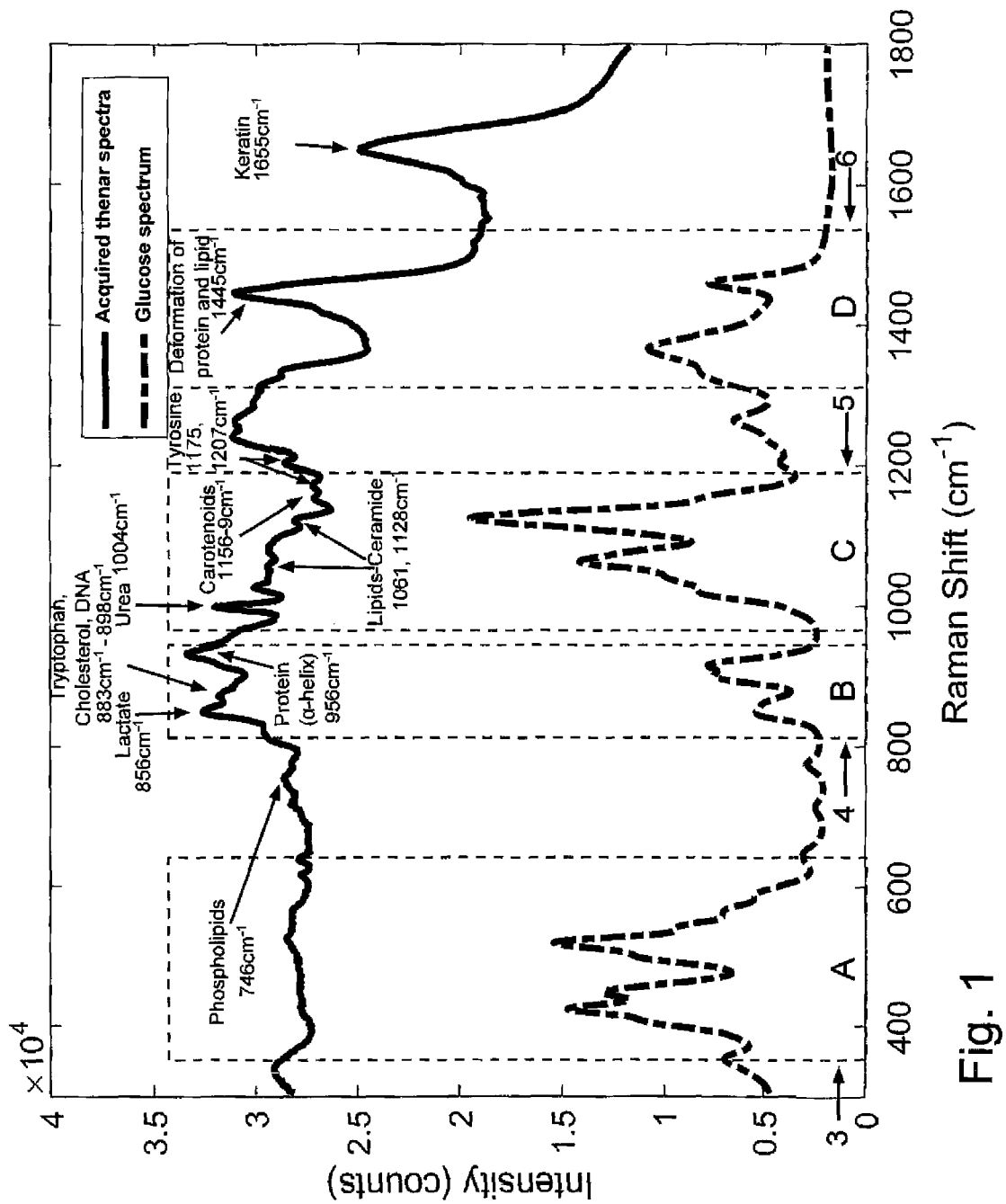
FIG. 1 is a schematic representation of a Raman shift spectrum for an irradiated sample of skin.

FIG. 1 shows the Raman spectrum obtained from a measurement subject. The data derives from the Raman spectroscopic study of the thenar region of a subject. Light was irradiated onto the subject's thenar region and the detected spectrum 1 is shown in FIG. 1. FIG. 1 also includes the Raman glucose spectrum 2 and so the Raman spectrum obtained from a measurement subject can be used to determine a concentration of glucose in the region of testing. The thenar Raman spectrum includes contributions from whatever molecules, are present in the region of testing and so it is necessary to determine from this the actual concentration of glucose.

It will be noted that the glucose spectrum includes four main regions of increased intensity which are labelled A to D and enclosed by boxes 3 to 6. Thus these regions in the thenar spectrum 1 will contain a relatively higher level of information regarding the glucose concentration in the sampled region than other parts of the spectrum 1.

It has been recognised that if the output from the spectrometers are arranged such as to resolve parts of the spectrum where high sensitivity/low noise is needed to a higher level than others then it will be possible to obtain a high quality signal whilst minimising the necessary use of expensive CCD detectors.

Spectral patterns A to D are identified where the most significant changes are due to the content of the glucose. The overall spectrum is then analysed in varying detail and in particular only the region where the most significant contributions from the content of the investigated analyte, are investigated at a high level of detail. This means that the other regions of the spectrum can be analysed, if at all, using simpler and low cost analysis mechanisms.

A method of high resolution and sensitivity can be designated to parts of the spectrum with a higher level of information and methods of lower resolution and sensitivity to parts of the spectrum where there is less information, thus reducing the complexity of a measurement set up significantly.

Figure 2:
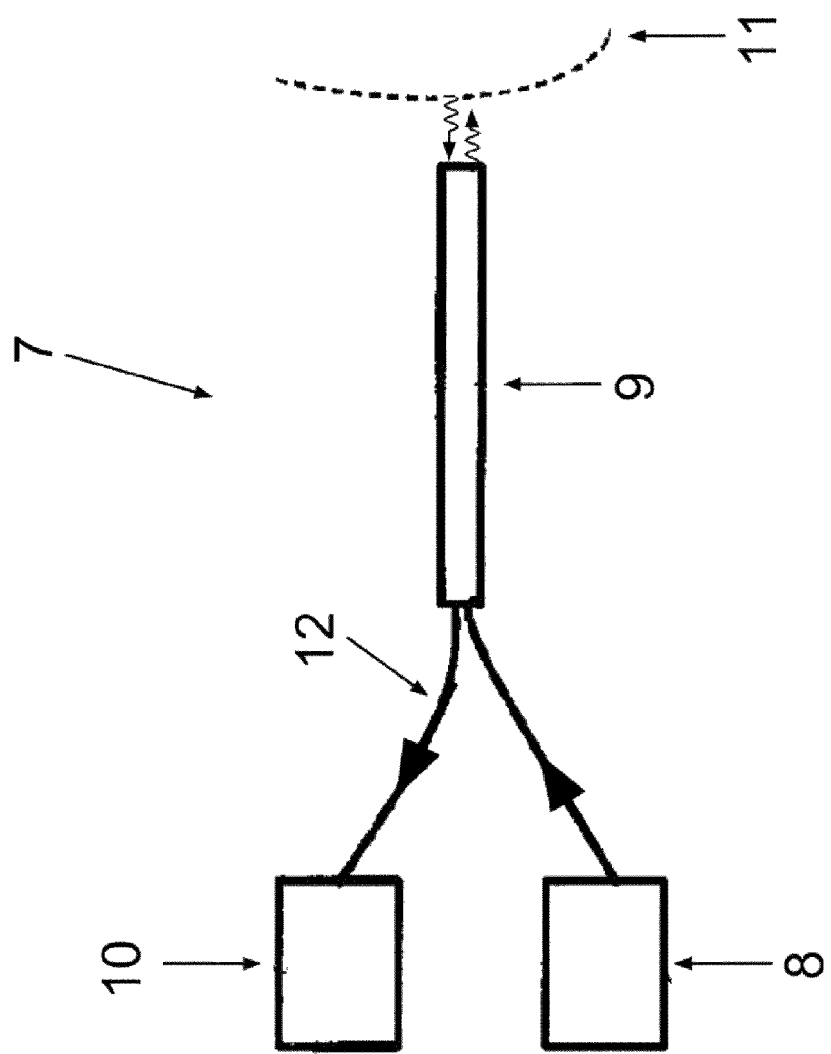
FIG. 2 is a schematic representation of an apparatus for analyte detection.

FIG. 2 shows a schematic representation of apparatus for measuring the glucose concentration subcutaneously and in vivo with the use of Raman spectroscopy. Although described herein with reference to detection and measurement of glucose levels, the method and apparatus could be used to measure the concentration of other analytes of interest.

The apparatus 7 comprises a light source 8, a probe 9 and a detector 10. The detector 10 will be described in greater detail below with reference to FIG. 3.

A subject 11 may be tested by engagement of the end of probe 9 with the surface of the skin. The mechanism for coupling the light from the source 8 to the skin 11 of the subject can be as described in detail in WO-A-2016/034448, already referred to above. Indeed, there are a number of known mechanisms for obtaining a Raman spectrum from a subject in vivo and any of the appropriate systems disclosed in the art could be used for this.

FIG. 2 shows schematically how light from the source 8 is coupled by the probe 9 to a subject 11 and then received by the probe 9 for communication to the analysis device 10. The analysis system 10 comprises a number of devices for light detection with possible dispersion elements as will be explained below. Each of the light detection devices is selected from a number of different types of light detection device so as to be capable of detecting the received signal at a desired level of resolution and signal to noise ratio. Within the system 10 there are at least two different types of light detection device thereby providing detection with a corresponding at least two levels of resolution and/or signal to noise ratio.

For example, in the regions A, B, C, D of the thenar spectrum 1 of FIG. 1, CCD-based spectrometers are used to resolve parts of the spectrum where high sensitivity and low noise is needed and a CMOS-based spectrometer may be used to resolve parts of the spectrum where high resolution is still needed, but a lower signal to noise ration can be tolerated.

When using an 830 nanometer laser as the excitation source, i.e. as the optical source 8 of FIG. 2, Raman spectrum is measured from 850 nanometers to 985 nanometers or from 283 to 1900 $cm^{-1}$.

Figure 3:
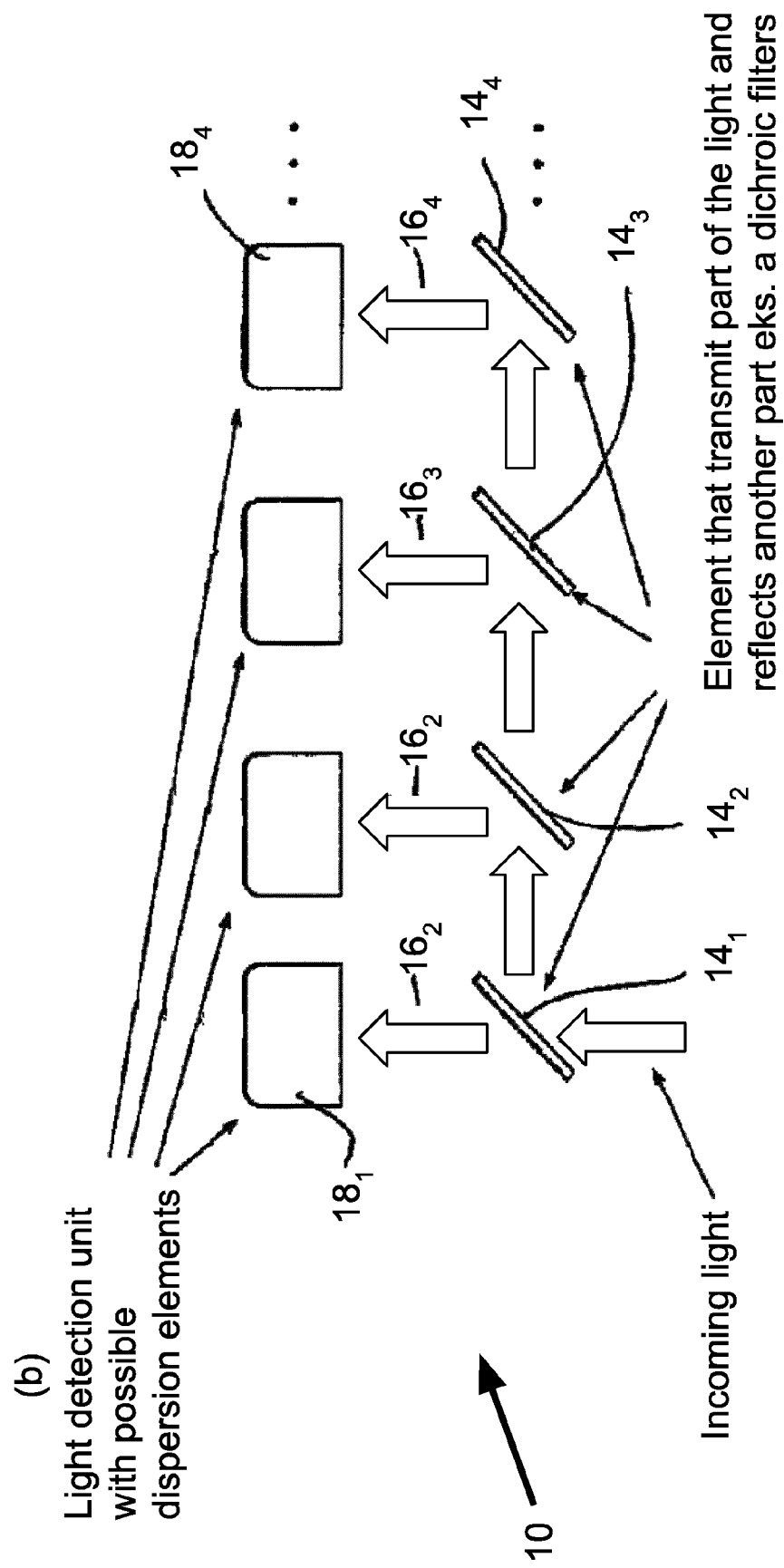
FIG. 3 is a schematic representation of the filtration structure for use in the apparatus of FIG. 2.

Referring to FIG. 3, a schematic representation of analysis system 10 is shown.

Light 12 is received as an input to the analysis system 10. A plurality of filtration devices $14_1$ to $14_4$ are provided. Each of the filtration elements $14_1$ to $14_4$ is arranged to transmit part of the light and reflect another part. Thus, the part of the light that each of the elements $14_1$ to $14_4$ transmits $16_1$ to $16_4$ represents a part of the spectrum selected in dependence on its frequency. A number of analysis devices $18_1$ to $18_4$ are provided each arranged to receive as an input the corresponding transmitted or reflected component from the filtration elements $14_1$ to $14_4$ in question. Thus, the apparatus has an inbuilt flexibility since the individual analysis devices or detection units $18_1$ to $18_4$ can be chosen to provide a desired level of resolution and/or signal to noise ratio for the corresponding part of the spectrum that it is arranged to receive.

In one example, the filtration elements $14_1$ to $14_4$ are each dichroic filters. In another example, they might be gratings or indeed any other wavelength dependent filtration device. In one example, at least two different types of filtration device are used, e.g. both dichroic mirrors and gratings are used for selecting different parts of the spectrum.

In a preferred embodiment, one or more of the analysis devices $18_1$ to $18_4$ includes a dispersion element. This is particularly useful for the regions expected to include the data relating to the analyte under investigation, as dispersing the received part of the spectrum will enable it to be analysed in more detail.

In FIG. 1, the boxes 3 to 6 indicate spectral regions with a high level of glucose information. The filtration elements $14_1$ to $14_4$ split the energy in dependence on frequency or wavelength into different detectors with various resolutions and noise floors. As an example, the spectral regions represented by boxes A to D which contain important Raman vibrations related to glucose, are preferably detected by a CCD-based spectrometer with 9 $cm^{-1}$ resolution.

Spectral regions outside the regions represented by the boxes A to D, could be detected by CMOS-based spectrometers with sufficient resolution, e.g. 25 $cm^{-1}$, just to estimate the signal slope over the frequency interval or alternatively, simply with photo diodes if only the average intensity needs to be estimated. Indeed, it could be that no detectors at all are provided for the regions outside the boxes where there is little information relating to glucose.

There is thus provided a system that enables selective analysis of different parts of a spectrum which enables more data to be derived about parts of the spectrum that are most important to the analysis in question, without the inefficiency of devoting to less important parts of the spectrum the same amount of resource. A required thorough level of analysis and investigation can be completed for the significant parts of the spectrum without wasting, time, effort, resource or cost on the less important parts. In the example given the glucose spectrum is shown superimposed on the thenar derived spectrum. This enables identification of the regions of interest of the thenar spectrum. if another metabolite or analyte is being investigated the windows of interest may well be at other positions on the spectrum In one example a spectrometer is used as at least one of the detection devices. For example, in a non-limiting embodiment wavelength-scale stationary-wave integrated Fourier-transform spectrometry (SWIFTS) is used. This SWIFS technology is described in detail in an article entitled Wavelength-Scale Stationary-Wave Integrated Fourier-Transform spectrometry by Le Coarer et al published in Nature Photonics, Vol. 1, August 2007, the entire contents of which are hereby incorporated by reference. More general Fourier Transform spectroscopy can also be used.

If the filtration elements are selectively and reconfigurably tunable then the system can be changed to focus on different parts of the spectrum in dependence on the metabolite or analyte being investigated. Thus, upon manufacture the filtration elements are tuned to desired frequencies such that the system as a whole is configured for analysis of a particular selected analyte.

Tunable filters or filtration devices can be any of a number of different types. Examples include filters that are tunable by variation in the angle of incidence (AOI) upon the filtration device. In such devices, the transmission window shifts with AOI relative to the filter normal. Examples include those produced by Semrock Inc (a part of IDEX Health and Science, LLC.) and viewable at, for example, https://www.semrock.com/versachrome-edge-tunabe-filters.aspx Other examples include those that are tuned by filter displacement (linear variable filters). In such filters, the transmission window shifts with respect to the lateral position of the filter. Examples include those produced by Delta Optical Thin Film A/S and viewable at for example, http://www.deltaopticalthinfilm.com/products/linear-variable-filters/

A further example would be acousto-optically (electrically) tunable filters, in which the refractive index of a crystal is modulated periodically by a high frequency acoustic wave generated by a piezoelectric transducer. In such devices, the frequency of the wave produced by the piezoelectric transducer determines the refractive index modulation period, and thereby the wavelength of diffracted light. Examples include those viewable at, for example, http://www.olympusmicro.com/primer/techniques/confocal/aotfintro.html.

Referring again to the example of FIG. 1, light from 0 to 280 $cm^{-1}$ is filtered out using a dichroic mirror and light with the spectral range 283 $cm^{-1}$ to 1900 $cm^{-1}$ passes through. This light is then incident upon another set of filters/dichroic mirrors that guide the spectral part to suitable spectrometers and/or detectors. Thus, a filter stack is arranged to separate the light in well-defined spectral parts so that different methods of analysis can be applied to the different parts.

In the example described, the apparatus is arranged to use Raman spectroscopy to determine the level of glucose in a sample. As already mentioned, the apparatus and method can be used irrespective of the analyte being measured. Other examples include one or more of lactate, fatty acids, urea, carbamide, cholesterol, or hemoglobin. FIG. 1, which shows a Raman spectrum has indicated on it other molecules that are known to have Raman peaks at certain wavelengths or shifts. Accordingly if other of these are to be primarily analysed, the analysis devices arranged to receive the significant part or parts of the spectrum will be selected to be high resolution and high SNR.

Embodiments of the present invention have been described with particular reference to the examples illustrated. However, it will be appreciated that variations and modifications may be made to the examples described within the scope of the present invention.

The invention claimed is:

1. An analyte detection apparatus, comprising:
a radiation source for irradiating a sample, and
a receiver, to receive an optical Raman spectrum of radiation transmitted back from the sample in response to the received radiation from the radiation source, the optical Raman spectrum including one or more parts of significance to an analyte to be detected and one or more parts not of significance to an analyte to be detected,
wherein the receiver comprises a plurality of different types of analysis device each arranged to receive a selected part of the received Raman optical spectrum transmitted back from the sample
wherein the different types of analysis device include at least one analysis device which has resolution and/or signal to noise ratio for detecting a part of the spectrum of significance to the analyte to be detected and at least one second type of analysis device which provides lower resolution and/or lower signal-to-noise ratio, for detecting a part of the spectrum not of significance to the analyte to be detected.

2. An apparatus according to claim 1, comprising one or more filtration devices arranged to filter the received optical spectrum and direct designated components to particular ones of the plurality of different types of analysis devices.

3. An apparatus according to claim 1, wherein the filtration devices include at least one tunable filtration device.

4. An apparatus according to claim 3, wherein the tunable filtration device comprises one or more of mechanically tuned filtration devices, electrically tuned filtration devices and acousto-optically tuned filtration devices.

5. An apparatus according to claim 1, wherein the different analysis devices include at least one CCD-based spectrometer.

6. An apparatus according to claim 5, wherein the different analysis devices include at least one CMOS-based spectrometer.

7. An apparatus according to claim 6, wherein one or more of Fourier-wave Spectrometry and Stationary Wave Integrated Fourier Transform Spectrometry are used.

8. An apparatus according to claim 1, wherein one or more of the selected parts of the received Raman optical spectrum is coupled to a dispersion member.

9. An apparatus according to claim 1, wherein the apparatus is arranged to determine concentration of an analyte.

10. An apparatus according to claim 9, wherein the analyte is selected from the group including glucose, lactate, fatty acids, urea, carbamide, cholesterol, alcohol and hemoglobin.

11. A method of detecting an analyte, the method comprising:
irradiating a sample with optical radiation from a radiation source;
receiving an optical Raman spectrum of radiation transmitted back by the sample in response to the received radiation from the radiation source, the optical Raman spectrum including one or more parts of significance to an analyte to be detected and one or more parts not of significance to an analyte to be detected, and
selectively coupling different parts of the received Raman spectrum to different analysis devices wherein the different analysis devices include at least one analysis device which has resolution and/or signal to noise ratio for detecting a part the spectrum of significance to the analyte to be detected and at least one second type of analysis device which provides lower resolution and lower signal-to-noise ratio, for detecting a part of the spectrum not of significance to the analyte to be detected.

12. A method according to claim 11, further comprising filtering the received spectrum into two or more components and coupling a first of the components to a first analysis device and a second of the components to a second analysis device.

13. A method according to claim 12, wherein the first analysis device is a CCD-based spectrometer.

14. A method according to claim 13, wherein the second analysis device is a CMOS-based spectrometer.

15. A method according to claim 14, wherein one or more of Fourier-wave Spectrometry and Stationary Wave Integrated Fourier Transform Spectrometry are used.

16. A method according to claim 11, wherein one or more of the selected parts of the received Raman optical spectrum is coupled to a dispersion member.

17. A method according to claim 11, further comprising determining the concentration of an analyte.

18. A method according to claim 17, wherein the analyte is selected from the group consisting of glucose, lactate, fatty acids, urea, carbamide, cholesterol, alcohol and hemoglobin.

* * * * *